United States Patent [19]

Chauvin et al.

[11] 4,371,627

[45] Feb. 1, 1983

[54] PROCESS FOR THE CATALYTIC SYNTHESIS OF METHANE BY REACTING HYDROGEN WITH CARBON MONOXIDE

[75] Inventors: Yves Chauvin, Le Pecq; Dominique Commereuc, Meudon; André Sugier, Rueil-Malmaison, all of France

[73] Assignee: Institut Francais du Petrole, Rueil-Malmaison, France

[21] Appl. No.: 307,150

[22] Filed: Sep. 30, 1981

[30] Foreign Application Priority Data

Sep. 30, 1980 [FR] France ............................ 80 21000

[51] Int. Cl.³ .............................................. C07C 1/04
[52] U.S. Cl. .................................. 518/700; 252/430; 252/431 R

[58] Field of Search ............................................ 518/700

[56] References Cited

U.S. PATENT DOCUMENTS 4,207,249 6/1980 Chauvin et al. .................... 518/700

Primary Examiner—Howard T. Mars
Attorney, Agent, or Firm—Millen & White

[57] ABSTRACT

Methane is obtained by reacting hydrogen with carbon monoxide in the presence of a catalyst manufactured by reacting a nickel compound with a reducing aluminum compound in the presence of a titanium compound. The aluminum compound is preferably a trialkylaluminum compound and the atomic ratio of aluminum to (nickel + titanium) is preferably from 1/1 to 20/1.

14 Claims, No Drawings

PROCESS FOR THE CATALYTIC SYNTHESIS OF METHANE BY REACTING HYDROGEN WITH CARBON MONOXIDE

BACKGROUND OF THE INVENTION

The object of the present invention is a process for synthesizing methane from hydrogen and carbon monoxide.

It has long been known that methane can be produced with a high selectivity by contacting carbon monoxide and hydrogen with a nickel-based catalyst. This reaction has been more particularly applied, up to now, to the removal of small amounts of carbon monoxide remaining in the hydrogen produced by steam-reforming or partial oxidation of a hydrocarbon fraction.

However, in view of a possible shortage of power resources, the manufacture of methane as a substitute for natural gas has gained interest.

The main difficulty to overcome, when reacting carbon monoxide with hydrogen, is the removal of heat produced by this strongly exothermic conversion.

The conventional use of fixed bed solid catalysts being not favorable to the heat exchange, can lead to local overheatings detrimental to the activity and life time of the catalyst. The process using a heterogeneous catalyst maintained suspended in a non-volatile liquid phase could be applied in that case. This technique has been described, for example, in the U.S. Pat. No. 3,989,734. Although resulting in a better heat exchange, this technique has a lower yield, due to a poorer diffusion of the reactants towards the catalyst, attributable to the presence of the liquid phase.

This explains why it has been proposed, for example in the French Pat. No. 2 374 280, to prepare catalytic systems soluble in an inert liquid medium which can be used thereafter as reaction medium or component of the reaction medium. The homogeneity of the catalyst solution guarantees, on the one hand, a good heat diffusion, thus an efficient removal of the reaction heat, and, on the other hand, a good chemical diffusion, thus a good accessibility of the reatants to the catalyst.

The soluble catalytic system, used in the above French patent, is obtained by admixing and reacting at least one constituent A with at least one constituent B in an inert liquid medium. The constituent A of the catalyst is a nickel compound and the constituent B a reducing aluminum compound.

These catalytic systems have however the disadvantage, when used in a continuous operation, to lose slowly their activity, in the course of time, which results in a high catalyst consumption.

SUMMARY OF THE INVENTION

It has surprisingly been found, and this is the object of the present invention, that the association of at least one nickel compound (constituent A) with at least one reducing aluminum compound (constituent B) and at least one titanium compound (constituent C), leads to a catalyst composition which retains a far better stability in the course of time, when it is used in a continuous operation, and which has an even higher activity.

DETAILED DISCUSSION

Examples of nickel compounds which can be used as the constituent A of the catalyst are nickel acetylacetonate, nickel sulfonates or alkylsulfonates, nickel salicylate and, more particularly, nickel carboxylate derivatives from fatty acids comprising at least 6, for example 6 to 40 and preferably 6 to 20 carbon atoms, for example nickel 2-ethyl hexanoate, nickel stearate, nickel oleate or the nickel salts of a fatty acid mixture, for example a mixture of fatty acids with 8, 9 and 10 carbon atoms, whose solubility in a hydrocarbon medium is good.

The reducing aluminum compound (the constituent B of the catalyst) is of the formula Al $R_3$ where at least one of the R radicals is a monovalent hydrocarbon radical, the other R radicals being hydrogen, a monovalent hydrocarbon radical and/or an alkoxy radical. The monovalent hydrocarbon radical and the alkoxy radical have preferably from 1 to 12 carbon atoms. A trialkylaluminum is however preferred, for example, trimethylaluminum, triethylaluminum, triisobutylaluminum or diisobutylaluminum hydride.

The titanium compound (the constituent C of the catalyst) can be selected among the tetravalent and trivalent titanium compounds complying with the general formula Ti $X_n$, where n is 3 or 4. The radicals X, which may be same or different, are electronegative moieties, for example, halide moieties, such as the chloride, bromide or iodide moiety, alkoxy groups comprising preferably from 1 to 18 carbon atoms, or acetylacetonate groups. Non-limitative examples are: titanium tetrachloride, titanium tetrakis 2-ethylhexylate, titanium tetrakis isopropylate, titanium tetrakis stearylate and titanium tris-acetylacetonate.

The liquid medium where the constituents A, B and C are admixed is generally used subsequently as reaction medium or component of this reaction medium. It must exhibit both properties of chemical inertia and thermal stability. Good results are obtained, in this respect, with saturated hydrocarbons, particularly with paraffinic hydrocarbons, which are liquid in the reaction conditions, for example with heptane, octane, dodecane, hexadecane or with mixtures of these hydrocarbons, for example with oil fractions or liquid paraffin fractions made free, if necessary, of the components which could poison the catalyst.

The catalyst can also be prepared in a liquid medium differing from that used later as the liquid reaction medium. In that case, this liquid may be without disadvantage relatively volatile and can be eliminated in the course of the methanation reaction or earlier.

This invention is not limited to the use of a particular reaction medium. All those proposed in the past literature and patents can also be used, provided they are compatible with the catalyst used and sufficiently stable in the reaction conditions.

The two constituents A and C of the catalytic system are supplied in such proportions that the titanium amount, expressed as titanium metal, be from 1 to 50% by weight of the aggregate (titanium metal + nickel metal), and preferably from 5 to 30% by weight.

The constituent B of the catalytic system is more advantageously admixed in such proportions that the atomic ratio aluminum/(nickel + titanium) be from 1/1 to 20/1. The preferred ratios are from 2/1 to 10/1.

When manufacturing the catalyst, the constituents A, B and C are admixed in an inert liquid, by supplying the reactants separately or in admixture, in any order. A preferred embodiment is described hereinafter.

The constituents A and C of the catalyst are dissolved in a hydrocarbon solvent under a non-oxidizing atmosphere, for example in an inert nitrogen or argon atmosphere, or again in a hydrogen atmosphere. If necessary the solvent is previously dried and de-aerated. A fairly volatile solvent is preferred, for example, hexane, benzene, heptane or toluene. The constituent B is added slowly thereafter, also in a non-oxidizing atmosphere. The admixing generally results in a gas release and a strong heat evolution. It is preferred that, in the course of this manufacture, the temperature of the reaction medium be maintained between 0° and 200° C., and advantageously from 20° to 150° C. The heavier solvent, for example a liquid paraffin, which will be used in the methanation reaction, is then added and the light solvent is withdrawn by vacuum evaporation.

The admixing of the constituents A, B and C may be effected either directly in the methanation reactor or, more easily, in a separate apparatus of, for example, glass. It is then, in a further stage, transferred into the reactor, while taking care to maintain it substantially protected from air and humidity. Traces of air or humidity may however, in some cases, not be particularly detrimental, or even may have a catalytic effect.

The resultant catalyst appears as a solution of homogeneous aspect and dark brown color which can be handled with a syringe or a pump when, for example, transferred into the reactor.

The composition of the synthesis gas mixture, expressed as the hydrogen/carbon monoxide molar ratio, is usefully selected from 0.05/1 to 10/1, preferably 0.7/1 to 4/1. The operation is preferably conducted with a ratio of about 3/1, which corresponds to the theoretical stoichiometrical ratio of the reaction.

The pressure of the synthesis mixture of hydrogen with carbon monoxide may vary from the atmospheric pressure up to 200 bars (20 M Pa) or more. The preferred operating pressure is from 5 to 70 bars (0.5 to 7 M Pa).

The hourly space velocity (VVH), expressed as the volume of synthesis gas mixture under normal conditions per volume of reactor and per hour, may vary from 1 to 10,000. The preferred VVHs are from 50 to 5,000.

The reaction temperature may be selected from 100° to 450° C., preferably from 200° to 350° C. The lower limit is dependent to a certain extent, on the selected hydrogen/carbon monoxide ratio and pressure. It is effectively preferred to select the operating conditions outside of the nickel tetracarbonyl stability zone, and preferably above this stability zone. By way of example, when operating with a hydrogen/carbon monoxide molar ratio of 3/1 and at a pressure of about 10 bars, the preferred temperature is above 200° C.

For this reason, it is preferred, when starting the heating or stopping the reactor, to scavenge the latter with a gas mixture totally free of carbon monoxide, for example, with pure hydrogen or a mixture of hydrogen with an inert gas.

The following examples illustrate the present invention and must not be interpreted as limiting it in any respect. Some results obtained with a titanium-free catalytic system are also given for comparison.

The reactor used in the following experiments is part of a micropilot unit operated continuously. The reactor consists of a stainless steel pipe of 2 cm internal diameter and 100 cc volume. It is fed with 40 cc of catalyst solution. The synthesis gas mixture is injected from the bottom of the reactor through a fritted material facilitating its diffusion throughout the medium, which results in a volume expansion. The gas is passed through a separator to decant possible liquid fractions and a portion of the reaction water; it is finally expanded and collected in a gas-meter to be analyzed thereafter.

EXAMPLES 1 TO 5

3.45 g of nickel 2-ethyl hexanoate having a 13% b.w. nickel content, 0.29 g of titanium tetrakis-isopropylate and 50 cc of benzene distilled and degassed in argon are introduced into a 250 cc glass vessel under argon atmosphere. Stirring is performed at room temperature to dissolve the two metal salts. 3.55 cc of triethylaluminum are then slowly added through a syringe. The heating produced by the reaction is moderated by immersing the flask in a water-bath to maintain the temperature of the mixture below 50° C.; the solution turns quickly dark brown and presents a homogeneous appearance. Stirring is continued for 30 minutes after the end of the triethylaluminum addition.

The proportions of the three constituents which have been employed correspond to the ratios:

$$\frac{Ti}{Ni + Ti} \text{ (by weight)} = 10\%$$

$$\frac{Al}{Ni + Ti} \text{ (by g-atom)} = \frac{3}{1}$$

The benzenic solution of catalyst is then withdrawn and admixed with 40 cc of liquid paraffin previously degassed under vacuum at 80° C. Benzene is then scavenged by stirring slowly the mixture in vacuo and the catalyst solution is then transferred into the steel reactor, as herein before described, under argon atmosphere.

A synthesis gas having a $H_2/CO$ ratio of 3.2/1 by volume is then injected in the operating conditions detailed in Table I. Each example of this Table relates to a 6-hour continuous run, the whole representing a 30-hour cycle.

The results obtained in each example are expressed as:

the conversion C, in % by mole, defined by the relation:

$$C (\%) = \frac{CH_4 + 2C_2H_6 + 3C_3H_8 + 4C_4H_{10} + CO_2}{CO \text{ (inlet)}} \times 100$$

the selectivity $S_{HC}$ to hydrocarbons, in % by mole, defined by the relation:

$$S_{HC} (\%) = \frac{CH_4 + 2C_2H_6 + 3C_3H_8 + 4C_4H_{10}}{CH_4 + 2C_2H_6 + 3C_3H_8 + 4C_4H_{10} + CO_2} \times 100$$

the selectivity $S_{CH_4}$ to methane, in % by mole, defined by the relation:

$$S_{CH_4} (\%) = \frac{CH_4}{CH_4 + 2C_2H_6 + 3C_3H_8 + 4C_4H_{10}} \times 100$$

The maximum activity A of the catalyst is estimated in the conditions of example 3 by means of the relation:

$$A = \frac{D_e \times C \times S_{HC} \times S_{CH_4}}{p \times (r + 1) \times 24} \text{ (mole } CH_4/g \text{ Ni/h)}$$

wherein

De is the gas feed rate in liters (NTP)/h,
p is the weight of nickel metal in the reactor,
r is the H$_2$/CO ratio by volume
C, S$_{HC}$ and S$_{CH_4}$ are as herein before defined.

This activity amounts here to 0.063 mole CH$_4$/g Ni/h.

The stability ΔC, in the course of time, of the catalyst is estimated by the difference between the hydrocarbon yields of example 2 and example 5 which have been conducted in the same conditions. It is expressed by the relation:

$$\Delta C = \frac{(C \times S_{HC})_5 - (C \times S_{HC})_2}{(C \times S_{HC})_2} \times 100$$

A positive value is indicative of a yield increase and a negative value of a loss of activity. ΔC of the tested catalyst is −7.9%, which shows that the loss of activity has been 7.9% in 24 h of run.

TABLE 1

| Example No. | T °C. | P bars | De l/h | Total run time | C % | S$_{HC}$ % | S$_{CH_4}$ % | Remarks |
|---|---|---|---|---|---|---|---|---|
| 1 | 230 | 10 | 11.3 | 6 h | 24.0 | 92.4 | 24.5* | *due to starting of the catalyst |
| 2 | 280 | 10 | 8.9 | 12 h | 18.1 | 100 | 83.9 | |
| 3 | 320 | 10 | 8.3 | 18 h | 41.7 | 86.5 | 95.5 | |
| 4 | 280 | 10 | 24.7 | 24 h | 9.7 | 100 | 70.8 | |
| 5 | 280 | 10 | 9.2 | 30 h | 22.4 | 74.4 | 74.6 | |

EXAMPLES 6
(comparison)

A titanium-free catalyst has been prepared substantially in the same manner as the catalyst of examples 1 to 5, the atomic ratio Al/Ni being always 3/1. The amount of catalyst, expressed as the weight of Ni metal introduced into the methanation reactor, was substantially unchanged. The catalyst has been subjected to the same cycle of tests as used in examples 1 to 5.

The maximum activity A determined in the same conditions as with the titanium-containing catalyst has been 0.057 mole CH$_4$/g Ni/h. The stability ΔC in the course of time, determined as above, has been −25.5%, i.e. a substantially greater loss of activity.

EXAMPLES 7 TO 10

The examples 1 to 5 have been repeated with the use of other nickel, titanium and aluminum compounds for the manufacture of the catalyst, the proportions $$\frac{Ti}{Ni + Ti} \text{ and } \frac{Al}{Ni + Ti}$$

being the same as in the above examples.

Example 7: nickel oleate + titanium tetrakis-butylate + triisobutylaluminum.

Example 8: nickel laurate + titanium tetrakis-stearylate + triethylaluminum.

Example 9: nickel salt of a mixture of fatty acids with 8-10 carbon atoms + titanium tris-acetylacetonate + diisobutylaluminum hybride.

Example 10: nickel acetylacetonate + titanium tetrakis-isopropylate + triethylaluminum.

The results of Table 2 have been obtained.

TABLE 2

| Example No. | Activity A | Stability ΔC |
|---|---|---|
| 7 | 0.055 | −10% |
| 8 | 0.058 | −9% |
| 9 | 0.062 | −12% |

TABLE 2-continued

| Example No. | Activity A | Stability ΔC |
|---|---|---|
| 10 | 0.060 | −8% |

What is claimed is:

1. In a process for manufacturing methane by reacting hydrogen with carbon monoxide in an inert liquid hydrocarbon medium, in the presence of a catalyst manufactured by reacting at least one nickel compound with at least one reducing aluminum compound in an inert liquid hydrocarbon medium, the improvement wherein said catalyst is the product obtained by reacting said nickel compound with said reducing aluminum compound in the presence of at least one hydrocarbon-soluble titanium compound in a non-oxidizing atmosphere; wherein the amount by weight of titanium relative to the aggregate (nickel + titanium), expressed as the metals, is from 1 to 50%; and wherein the atomic ratio of aluminum/(nickel + titanium) is from 1/1 to 20/1.

2. A process according to claim 1, wherein the aluminum compound has the formula Al R$_3$ and wherein at least one R group is a monovalent hydrocarbon radical, each of the other R groups being hydrogen, a monovalent hydrocarbon radical or an alkoxy group.

3. A process according to claim 1, wherein the aluminum compound is a trialkylaluminum.

4. A process according to claim 1, wherein the nickel compound is a nickel carboxylate of a fatty acid, said fatty acid having at least 6 carbon atoms.

5. A process according to claim 1, wherein the titanium compound has the formula Ti X$_n$, where n is 3 or 4 and X is a halide, an alkoxy group or an acetylacetonate group.

6. A process according to claim 1, wherein the titanium compound is a tetrakis-alkoxy titanium.

7. A process according to claim 1, wherein the inert liquid comprises at least one saturated hydrocarbon.

8. A process according to claim 1, wherein the conditions of the reaction between hydrogen and carbon monoxide comprise a temperature of 100° to 450° C. and a pressure of 1 to 200 bars.

9. A process according to claim 8, wherein the reaction temperature is higher than the temperature at which nickel tetracarbonyl is stable.

10. A process according to claim 1, wherein said amount of titanium relative to the aggregate (nickel + titanium) is from 5 to 30% by weight.

11. A process according to claim 1, wherein said atomic ratio of aluminum/(nickel + titanium) is from 2/1 to 10/1.

12. A process according to claim 1, wherein the hydrogen/carbon monoxide molar ratio is from 0.7/1 to 4/1.

13. A process according to claim 8, wherein said pressure is 5-70 bars.

14. A process according to claim 5, wherein said titanium compound is titanium tetrachloride, titanium tetrakis 2-ethylhexylate, titanium tetrakis isopropylate, titanium tetrakis stearylate or titanium trisacetylacetonate.

* * * * *